(12) United States Patent
Fukutani et al.

(10) Patent No.: US 10,582,910 B2
(45) Date of Patent: Mar. 10, 2020

(54) INFORMATION ACQUISITION APPARATUS AND INFORMATION ACQUISITION METHOD

(71) Applicant: CANON KABUSHIKI KAISHA, Tokyo (JP)

(72) Inventors: Kazuhiko Fukutani, Yokohama (JP); Ryuichi Nanaumi, Tokyo (JP); Takuro Miyasato, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 413 days.

(21) Appl. No.: 15/384,898

(22) Filed: Dec. 20, 2016

(65) Prior Publication Data

US 2017/0181727 A1 Jun. 29, 2017

(30) Foreign Application Priority Data

Dec. 25, 2015 (JP) .................................. 2015-254372

(51) Int. Cl.
*A61B 8/00* (2006.01)
*A61B 5/145* (2006.01)
(Continued)

(52) U.S. Cl.
CPC .......... *A61B 8/4281* (2013.01); *A61B 5/0095* (2013.01); *A61B 5/14546* (2013.01);
(Continued)

(58) Field of Classification Search
CPC . A61B 5/0091; A61B 5/0095; A61B 5/14546; A61B 5/4312; A61B 5/748;
(Continued)

(56) References Cited

U.S. PATENT DOCUMENTS

2011/0257530 A1\* 10/2011 Tokita .................. A61B 5/0091
600/443
2013/0312526 A1\* 11/2013 Oishi ................... A61B 5/0095
73/620

FOREIGN PATENT DOCUMENTS

| CN | 102256537 A | 11/2011 |
| CN | 102256536 B | 10/2014 |
| CN | 105054971 A | 11/2015 |

OTHER PUBLICATIONS

Fakhrejahani, Elham, et al. "Clinical Report on the First Prototype of a Photoacoustic Tomography System with Dual Illumination for Breast Cancer Imaging." 127 Oct. 2015. PLoS One. vol. 10 Issue 10. 1-13. (Year: 2015).\*

(Continued)

*Primary Examiner* — Nadia A Mahmood
(74) *Attorney, Agent, or Firm* — Canon U.S.A., Inc., IP Division

(57) ABSTRACT

An information acquisition apparatus according to the present invention includes a container configured to store a deformable acoustic matching member, a receiving unit configured to receive an acoustic wave generated from an object and output a signal, and a processing unit configured to acquire object information based on the signal. The processing unit acquires sound speed information about the object, acquires sound speed information about the acoustic matching member, acquires positional information about the acoustic matching member, acquires propagation time information about the acoustic wave between an interesting position of the object and the receiving unit using the positional information, the sound speed information about the object, and the sound speed information about the acoustic matching member, and acquires the object information about the interesting position using the signal and the propagation time information.

16 Claims, 8 Drawing Sheets

(51) Int. Cl.
*A61B 5/00* (2006.01)
*A61B 8/08* (2006.01)

(52) U.S. Cl.
CPC .......... *A61B 8/5261* (2013.01); *A61B 8/5269* (2013.01); *A61B 5/0091* (2013.01); *A61B 5/4312* (2013.01); *A61B 5/748* (2013.01); *A61B 8/0825* (2013.01); *A61B 2562/08* (2013.01)

(58) Field of Classification Search
CPC ... A61B 8/0825; A61B 8/4281; A61B 8/5261; A61B 8/5269; A61B 2562/08
USPC ....................................................... 600/472
See application file for complete search history.

(56) References Cited

OTHER PUBLICATIONS

Fakhrejahani, E., et al., "Clinical Report on the First Prototype of a Photoacoustic Tomography System with Dual Illumination for Breast Cancer Imaging", Plos One, Oct. 27, 2015, pp. 1-13.
Xu, M., et al., "Universal back-projection algorithm for photoacoustic computed tomography", Physical Review E, 2005, pp. 016706-1-016706-7, vol. 71.

* cited by examiner

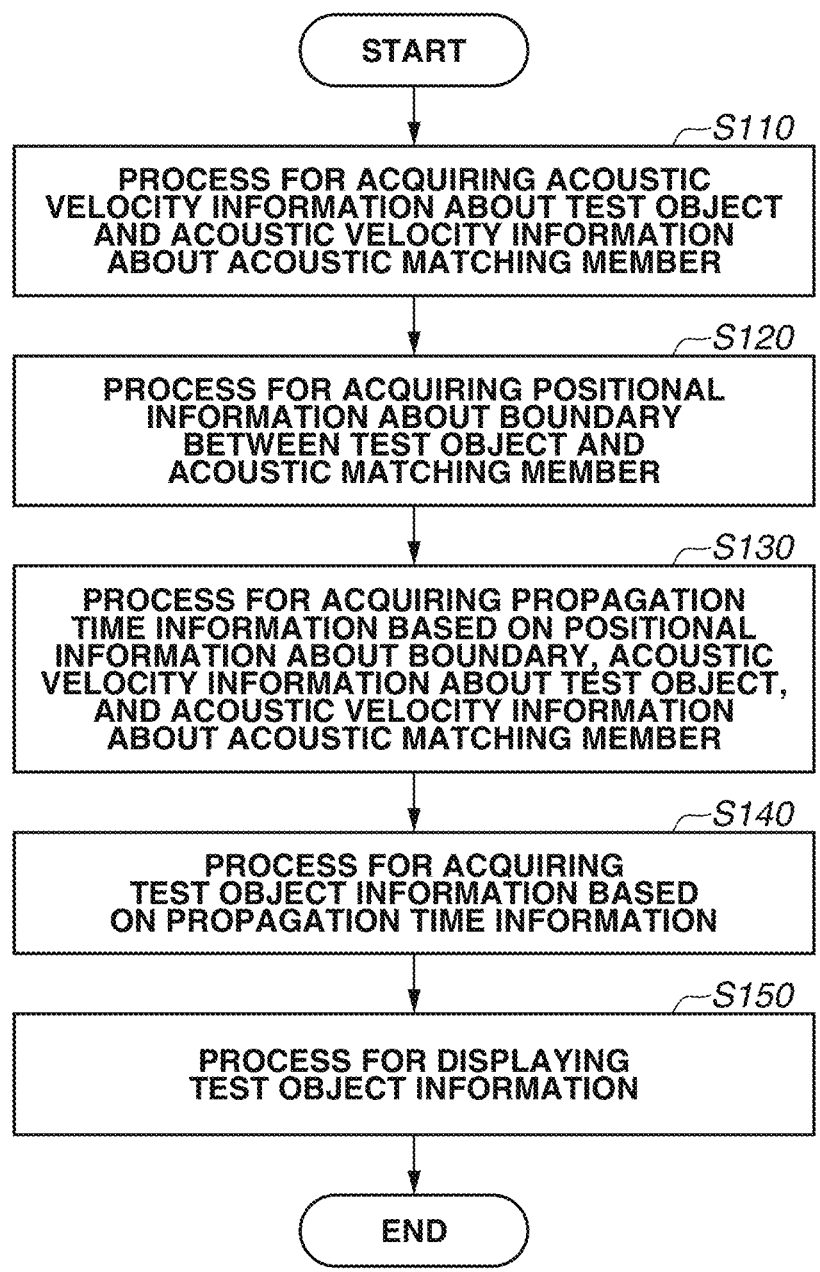

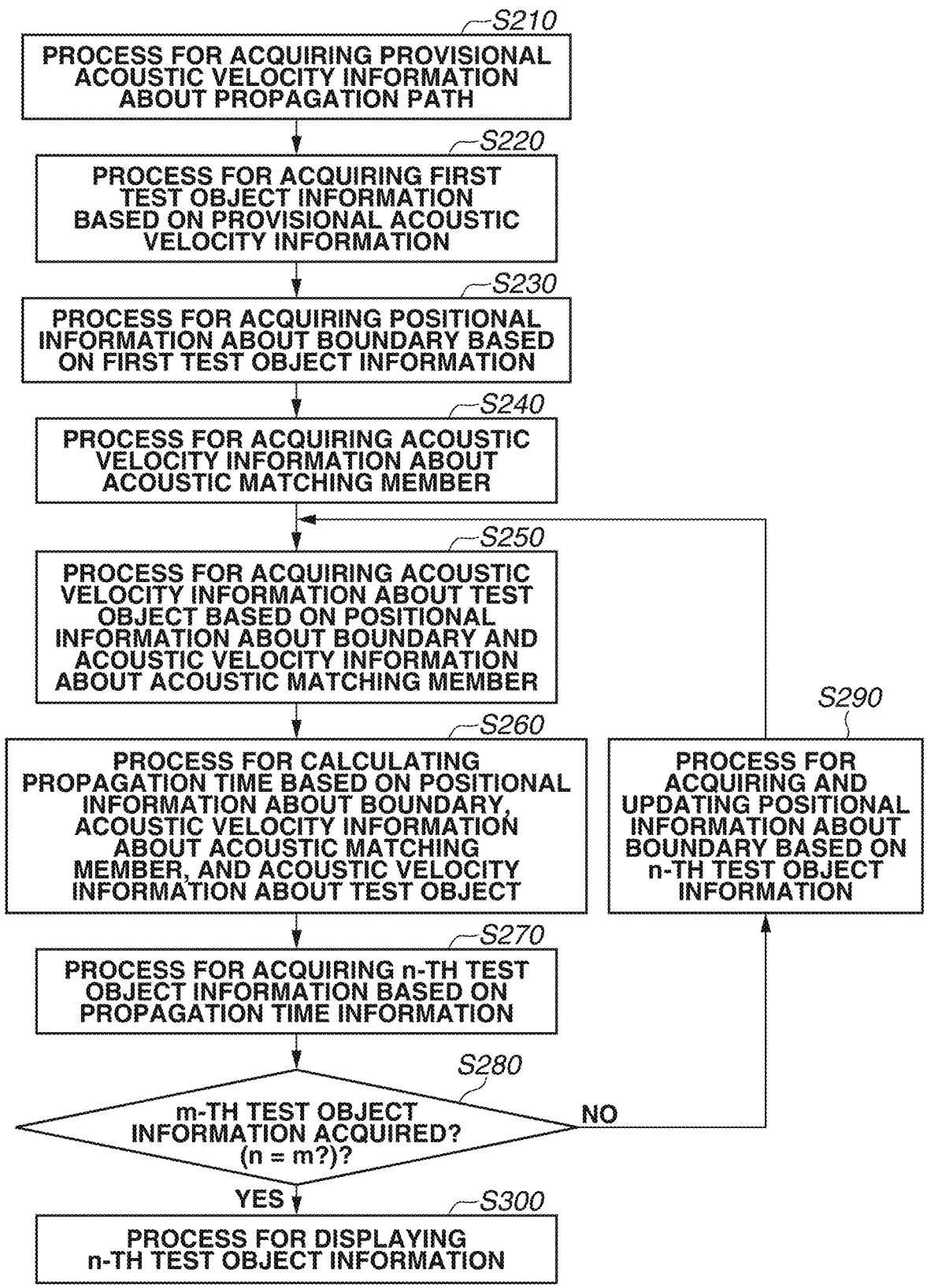

INFORMATION ACQUISITION APPARATUS AND INFORMATION ACQUISITION METHOD

BACKGROUND OF THE INVENTION

Field of the Invention

The present invention relates to an information acquisition apparatus that can acquire object information based on a signal originated from an acoustic wave.

Description of the Related Art

As a technique capable of acquiring internal information about a living organism or any other object by receiving an acoustic wave, an information acquisition apparatus, such as a photoacoustic imaging apparatus or an ultrasonic wave echo imaging apparatus, has been proposed.

As discussed in Minghua Xu and Lihong V. Wang, "Universal back-projection algorithm for photoacoustic computed tomography", PHYSICAL REVIEW E 71, 016706 (2005), there is a conventionally known time domain reverse projection method, which is generally referred to as "Universal Back-Projection." As discussed in Minghua Xu and Lihong V. Wang, "Universal back-projection algorithm for photoacoustic computed tomography", PHYSICAL REVIEW E 71, 016706 (2005), it is conventionally known to perform reconstruction by using a single sound speed under an assumption that a measurement target is a uniform medium.

However, in a case where an acoustic wave generated from an object (i.e., a measurement target) propagates a medium that is different from the object in sound speed, it is difficult to accurately acquire the object information according to the method discussed in Minghua Xu and Lihong V. Wang, "Universal back-projection algorithm for photoacoustic computed tomography", PHYSICAL REVIEW E 71, 016706 (2005), because a significant difference occurs in propagation time when the medium is different from the object in sound speed.

SUMMARY OF THE INVENTION

The present invention is directed to an information acquisition apparatus that can prevent the accuracy of object information from deteriorating due to a difference in propagation time caused by a medium that is different from an object in sound speed.

According to an aspect of the present invention, an information acquisition apparatus includes a container configured to store a deformable acoustic matching member, a receiving unit configured to receive an acoustic wave generated from an object and output a signal, and a processing unit configured to acquire object information based on the signal. The receiving unit is configured to receive the acoustic wave having propagated in the acoustic matching member. The processing unit acquires sound speed information about the object, acquires sound speed information about the acoustic matching member, acquires positional information about the acoustic matching member, acquires propagation time information about the acoustic wave between an interesting position of the object and the receiving unit using the positional information, the sound speed information about the object, and the sound speed information about the acoustic matching member, and acquires the object information about the interesting position using the signal and the propagation time information.

Further features of the present invention will become apparent from the following description of exemplary embodiments with reference to the attached drawings.

BRIEF DESCRIPTION OF THE DRAWINGS

FIG. 3 is a flowchart illustrating information acquisition processing according to the first exemplary embodiment.

FIG. 6 illustrates an exemplary flow of a processing method according to a second exemplary embodiment.

DESCRIPTION OF THE EMBODIMENTS

Figure 1:
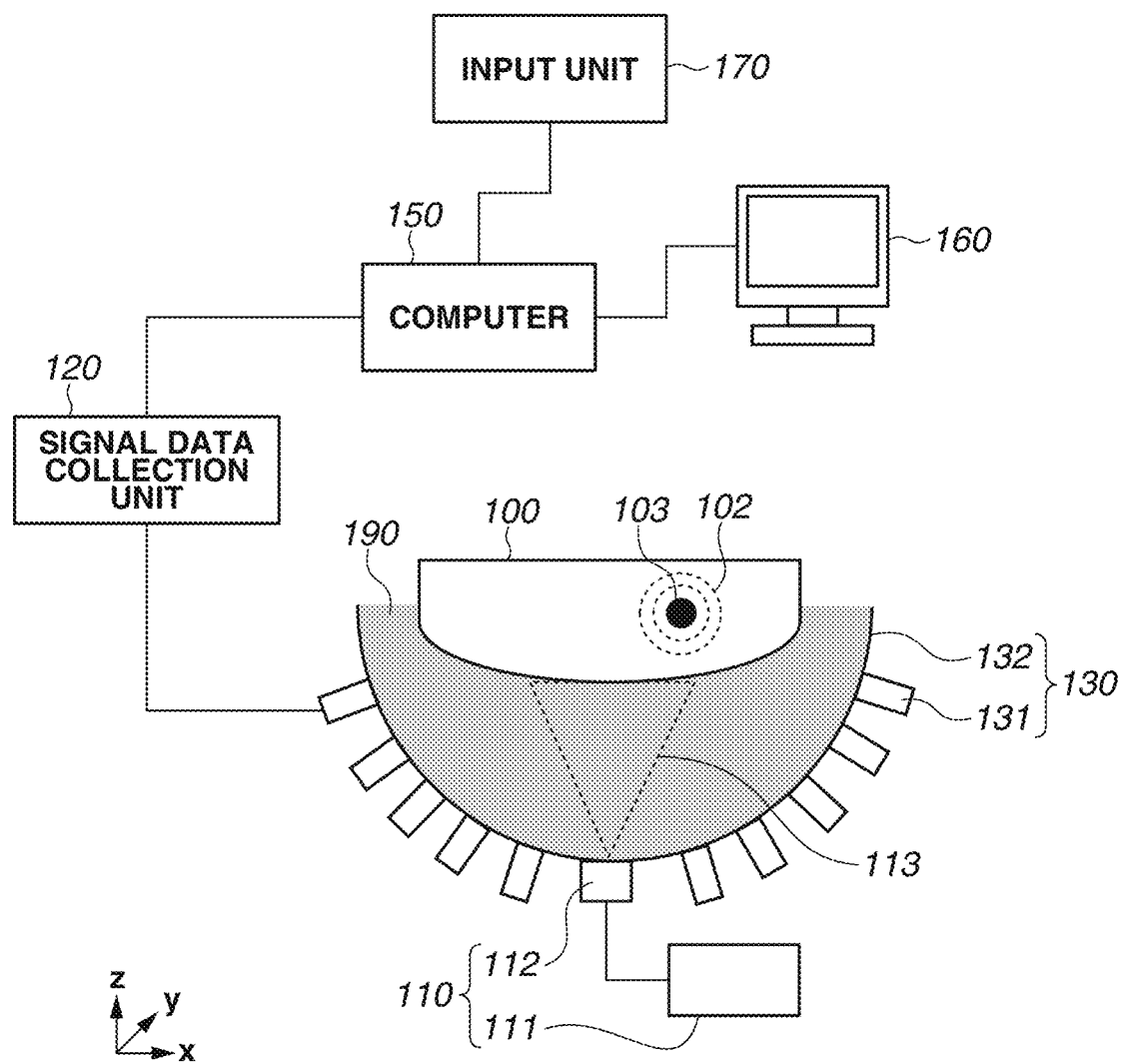
FIG. 1 schematically illustrates a photoacoustic apparatus according to a first exemplary embodiment.

Hereinafter, the present invention will be described in detail below with reference to attached drawings, in which the same constituent components are basically denoted by the same reference numerals, and descriptions thereof are omitted.

<Photoacoustic Apparatus>

An exemplary configuration of a photoacoustic apparatus according to a first exemplary embodiment will be described with reference to FIG. 1. The photoacoustic apparatus according to the present exemplary embodiment includes an optical illumination unit 110, a probe 130, a signal data collection unit 120, a computer 150, a display unit 160, and an input unit 170.

The optical illumination unit 110 can irradiate an object 100 with pulsed light 113 so that acoustic waves 102 can be generated in the object 100. The acoustic waves 102 derived from photoacoustic effects of the light can be generally referred to as "photoacoustic waves." The probe 130 can output an electric signal (analog signal) by receiving a photoacoustic wave 102. The signal data collection unit 120 can convert the electric signal (i.e., the analog signal) output from the probe 130 into a digital signal and can output the digital signal to the computer 150. The computer 150 can store the digital signal output from the signal data collection unit 120 as signal data having originated from the photoacoustic wave.

The computer 150 can generate image data representing information about the object 100 (i.e., object information) by performing signal processing on the stored digital signal. Further, the computer 150 can output the image data to the display unit 160 after performing image processing on the obtained image data. The display unit 160 can display an image of the information about the object 100. A physician (i.e., a user) can perform diagnosis by confirming the image relating to the information about the object displayed on the display unit 160.

The object information obtained by the photoacoustic apparatus according to the present exemplary embodiment includes at least one of photoacoustic wave generation sound pressure (initial sound pressure), light energy absorption density, optical absorption coefficient, and density of a substance constituting an object. The information relating to substance density is, for example, oxyhemoglobin density, deoxyhemoglobin density, total hemoglobin density, or degree of oxygen saturation. The total hemoglobin density is a sum of the oxyhemoglobin density and the deoxyhemoglobin density. The degree of oxygen saturation is the percentage of the oxyhemoglobin to the entire hemoglobin. The photoacoustic apparatus according to the present exemplary embodiment acquires image data representing a value of the above-mentioned information at each position (i.e., each position in a two-dimensional or three-dimensional space) of the object.

Hereinafter, an exemplary configuration of an information acquisition apparatus according to the present exemplary embodiment will be described in detail below.

(Optical Illumination Unit 110)

The optical illumination unit 110 includes a light source 111 that can emit the pulsed light 113 and an optical system 112 that can guide the pulsed light 113 emitted from the light source 111 to the object 100.

The pulse width of the light emitted from the light source 111 can be in a range from 1 ns from 100 ns. Further, the wavelength of the emitted light can be in a range from 400 nm to 1600 nm. If an imaging target is a blood vessel positioned adjacently to a surface of a living organism and a required resolution is high, it is desired to use the light having a wavelength not less than 400 nm and not greater than 700 nm that is expected to be greater in absorption at the blood vessel. On the other hand, if an imaging target is positioned at an inner (deeper) portion of a living organism, it is desired to use the light having a wavelength not less than 700 nm and not greater than 1100 nm that is expected to be smaller in absorption at a background tissue (e.g., water or fat) of the living organism.

The light source 111 can be configured to use a laser or a light-emitting diode. Further, if a plurality of beams mutually different in wavelength is required in the measurement, the light source 111 can be configured to convert the wavelength of light to be emitted. In a case where a plurality of beams having different wavelengths is used to irradiate the object, it is useful to prepare a plurality of light sources that can emit the beams mutually different in wavelength and cause respective light sources to alternately emit light. In the following description, it is assumed that the expression "light source" encompasses a plurality of light sources to be used collectively. The laser can be selected from various types of lasers, including a solid-state laser, a gas laser, a dye laser, and a semiconductor laser. For example, a pulsed laser (e.g., Nd: YAG laser or alexandrite laser) can be used as the light source 111. Further, a Ti: sa laser that uses an Nd: YAG laser beam as exciting light or an Optical Parametric Oscillators (OPO) laser can be used as the light source 111. Further, a microwave source can be used as the light source 111.

The optical system 112 can include various optical elements (e.g., lenses, mirrors, and optical fibers). If the object 100 is a breast, it is desired to widen the beam diameter of the pulsed light. Therefore, a light-emitting unit of the optical system 112 can be configured to include a diffuser capable of diffusing the light. On the other hand, if the photoacoustic apparatus is a photoacoustic microscope, it is desired to constitute the light-emitting unit of the optical system 112 by a lens so that a focused beam can be emitted to enhance the resolution.

Alternatively, the optical illumination unit 110 can be configured to directly irradiate the object 100 with the pulsed light 113 emitted from the light source 111, instead of including the optical system 112.

(Probe 130)

The probe 130, which serves as a receiving unit, includes a plurality of transducers 131 and a support member 132 that can support the transducers 131. Each transducer 131 can output an electric signal by receiving an acoustic wave.

The transducer 131 can be constituted, for example, by a piezoelectric ceramic material represented by lead zirconate titanate (PZT) or a macromolecular piezoelectric film material represented by polyvinylidene fluoride (PVDF). Further, an element other than the piezoelectric element is usable. For example, a capacitance type transducer, such as a capacitive micro-machined ultrasonic transducer (CMUT), or a transducer that uses a Fabry-Perot interferometer is employable. Further, any other transducer can be employed if it can generate an electric signal in response to reception of an acoustic wave. Further, the signal obtained by the transducer is a time-resolved signal. More specifically, the amplitude of a signal obtained by a receiving element represents a value derived from the sound pressure received by the transducer at each time (e.g., a value proportional to the sound pressure).

The frequency components of the photoacoustic wave are typically present in the range from 100 KHz to 100 MHz. Therefore, it is useful to employ a transducer capable of detecting these frequency components as the transducer 131.

The support member 132 can be constituted by a metallic material or a plastic material that is excellent in mechanical strength. In the present exemplary embodiment, the support member 132 has a semi-spherical shell shape, so that the plurality of transducers 131 can be supported on the semi-spherical shell thereof. In this case, a directional axis of each transducer 131 disposed on the support member 132 meets the center of curvature of the semisphere. If imaging is performed based on an electric signal group generated from the plurality of transducers 131, the image quality can be enhanced at or in the vicinity of the center of curvature. The support member 132 can be configured to have any other shape if it can support the transducers 131. The support member 132 can include a plurality of transducers arranged on a flat surface or a curved surface, which is referred to as 1D array, 1.5D array, 1.75D array, or 2D array.

Further, the support member 132 can function as a container that can store an acoustic matching member 190. More specifically, the support member 132 can be used as the container capable of storing and locating the acoustic matching member 190 between the transducer 131 and the object 100.

Further, the probe 130 can be configured to include an amplifier that can amplify a time series analog signal output from the transducer 131. Further, the probe 130 can be configured to include an A/D converter that can convert the time series analog signal output from the transducer 131 into a time series digital signal. More specifically, the probe 130 can be configured to include the signal data collection unit 120 described below.

It is desired to locate the transducers 131 in such a way as to surround the entire periphery of the object 100 so that the acoustic wave can be detected at various angles. However, in a case where the object 100 is so large that the transducers cannot surround the entire periphery of the object 100, the transducers can be arranged on a semi-spherical support member as illustrated in FIG. 1. It is useful to take the object into consideration in optimizing the total number and the layout of the transducers as well as the shape of the support member. The present invention does not limit an employable type of the probe 130.

(Signal Data Collection Unit 120)

The signal data collection unit 120 includes an amplifier that can amplify the electric signal (i.e., the analog signal) output from the transducer 131 and an A/D converter that can convert the analog signal output from the amplifier into a digital signal. The signal data collection unit 120 can be constituted, for example, by a "field programmable gate array" (FPGA) chip. The digital signal output from the signal data collection unit 120 can be stored in an appropriate storage device of the computer 150. The signal data collection unit 120 may be referred to as "data acquisition system" (DAS). In the following description, the electric signal includes both the analog signal and the digital signal. The signal data collection unit 120 is connected to a light detection sensor attached to a light-emitting portion of the optical illumination unit 110. The signal data collection unit 120 can be configured to start processing in synchronization with the pulsed light 113 emitted from the optical illumination unit 110.

(Computer 150)

The computer 150 includes a processing unit, a storage unit, and a control unit, functions of which will be described in detail below with reference to processing flows.

The storage unit can be constituted by a non-temporary storage medium, such as a read only memory (ROM), a magnetic disk, or a flash memory. Further, the storage unit can be constituted by a volatile medium, such as a random access memory (RAM). The storage medium that stores programs is a non-temporary storage medium.

The processing unit, i.e., a unit having arithmetic functions can be constituted by a processor, such as a central processing unit (CPU), a graphics processing unit (GPU), or a digital signal processor (DSP), or can be constituted by an arithmetic circuit, such as a field programmable gate array (FPGA) chip. The above-mentioned units can be constituted by a single processor or a single arithmetic circuit or can be constituted by a plurality of processors or a plurality of arithmetic circuits.

The control unit can be constituted by an arithmetic element (e.g., CPU). The control unit can control operations to be performed by respective constituent components of the photoacoustic apparatus. The control unit can control respective constituent components of the photoacoustic apparatus in response to instruction signals entered via the input unit 170 based on various operations (including a measurement start operation). Further, the control unit can read program codes from the storage unit and control the operations to be performed by respective constituent components of the photoacoustic apparatus.

The computer 150 can be constituted by a specially designed work station. Further, constituent components of the computer 150 can be different hardware devices. Further, the computer 150 can be constituted at least partly by a single hardware device.

Figure 2:
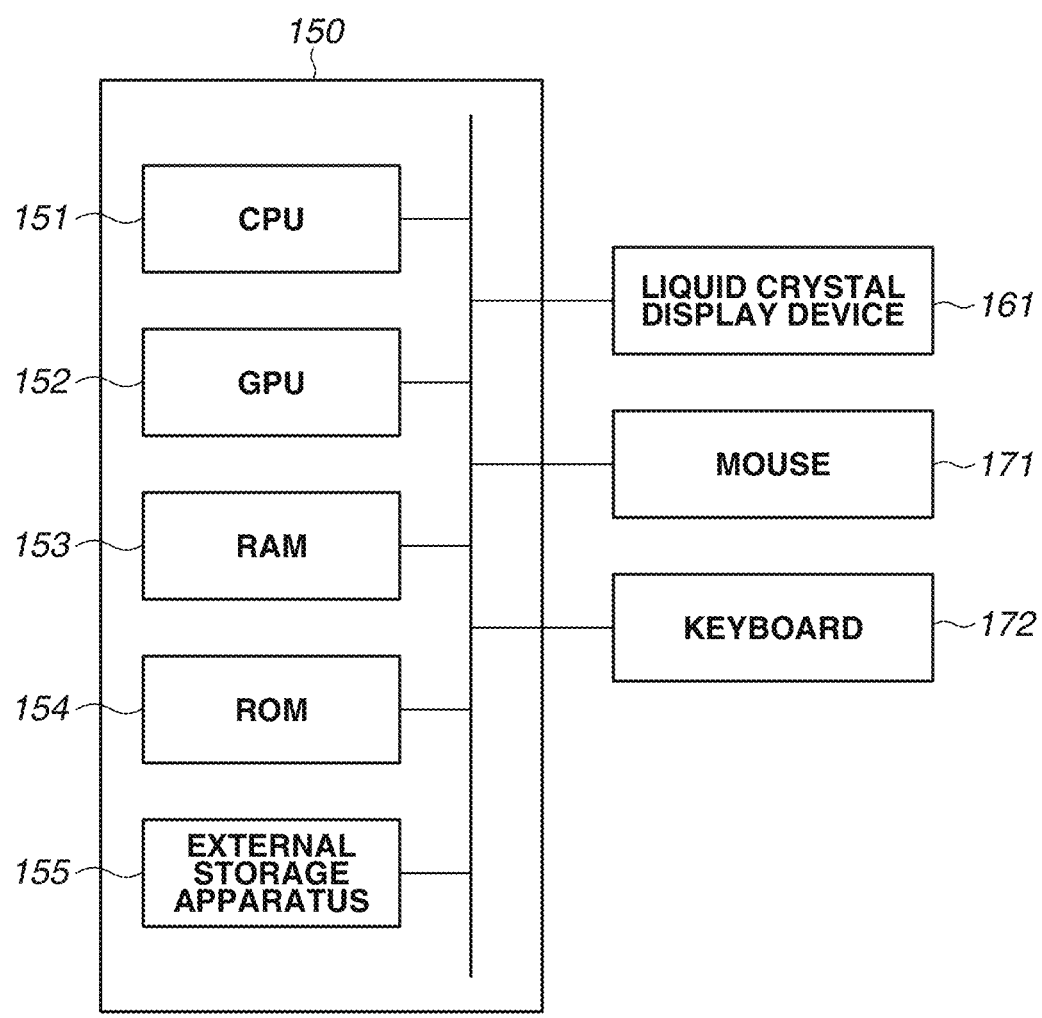
FIG. 2 illustrates a peripheral configuration of a computer.

FIG. 2 illustrates a practical configuration of the computer 150 according to the present exemplary embodiment. The computer 150 according to the present exemplary embodiment includes a CPU 151, a GPU 152, a RAM 153, a ROM 154, and an external storage apparatus 155. Further, the computer 150 is connected to a liquid crystal display device 161, a mouse 171, and a keyboard 172. The liquid crystal display device 161 is functionally operable as the display unit 160. The mouse 171 and the keyboard 172 are functionally operable as the input unit 170.

Further, the computer 150 and the plurality of transducers 131 can be housed in a common casing. In this case, the computer housed in the casing can be configured to perform a part of the signal processing and cause an external computer to perform the rest of the signal processing. In this respect, the computer according to the present exemplary embodiment includes both the internal and external computers provided on the inside and the outside of the casing.

(Display Unit 160)

The display unit 160 is, for example, a liquid crystal display device or an organic Electro Luminescence (EL). The display unit 160 can display images and numerical values representing specific positions based on object information obtained by the computer 150. The display unit 160 can be configured to display various kinds of images and GUIs that enable a user to operate the apparatus. In displaying the object information, the display unit 160 or the computer 150 can be configured to perform image processing (e.g., adjustment of luminance value) beforehand.

(Input Unit 170)

The input unit 170 can be constituted by a mouse and a keyboard that a user can operate. Further, the display unit 160 can include a touch panel and the display unit 160 can be configured as the input unit 170.

Respective constituent components of the photoacoustic apparatus can be separately constituted or can be integrated as a single apparatus. Further, at least a part of the photoacoustic apparatus can be constituted as a single apparatus.

(Acoustic Matching Member 190)

The acoustic matching member 190 is not included in the photoacoustic apparatus. The acoustic matching member 190 causes acoustic waves to propagate between the object 100 and the transducer 131. The acoustic matching member 190 is constituted by a deformable member, which deforms when it is brought into contact with the object 100. More specifically, the acoustic matching member 190 is deformable along the object in such a way as to reduce the clearance between the object 100 and the transducer 131 as much as possible. The acoustic matching member 190 can be a material that is small in acoustic wave attenuation. A member having appropriate acoustic impedance between acoustic impedance of the object 100 and acoustic impedance of the transducer 131 is employed as the acoustic matching member 190. In particular, a material similar to the object in acoustic impedance can be selected. When irradiation light travels in the acoustic matching member 190, it is desired that an employed material is transparent against the irradiation light. For example, the acoustic matching member 190 can be water or ultrasonic wave gel.

The acoustic matching member 190 according to the present invention is a fluid substance. Therefore, an appropriate container capable of holding and accommodating the acoustic matching member 190 is required. In the present exemplary embodiment, the support member 132 can serve as a container that stores the acoustic matching member 190. Alternatively, the information acquisition apparatus can be configured to include a special container that can store the acoustic matching member 190 and is provided between the transducers 131 and the object 100, in addition to the support member 132. The container can be a plastic container or a metallic container.

(Object 100)

The object 100 will be described in detail below, although it does not constitutes the photoacoustic apparatus. The photoacoustic apparatus according to the present exemplary embodiment is usable in the diagnosis of a malignant tumor or a blood vessel disease of a person or an animal or in the follow-up observation of a chemical treatment. In this case, the object 100 is a living organism, such as a breast, a neck region, or an abdominal region of a human body or an animal body, which will be a target portion in the diagnosis. For example, if the measurement target is a human body, oxyhemoglobin or deoxyhemoglobin, or a blood vessel including them, or a newborn blood vessel formed adjacently to a tumour can be a practical target of a light absorption member 103. Further, a plaque of a carotid wall can be another practical target of the light absorption member 103. Further, methylene blue (MB), indocyanine green (ICG) or any other dye, gold fine particles, or a foreign substance including integrated or chemically processed components thereof can be the light absorption member 103.

<Information Acquisition Method>

Next, exemplary signal processing that can be performed by the computer 150 will be described in detail below with reference to a processing flow illustrated in FIG. 3. The processing flow illustrated in FIG. 3 can be started after the computer 150 completes the storing of signal data originated from an electric signal obtained from the probe 130.

(Step S110: Process for Acquiring Sound Speed Information about Object and Sound Speed Information about Acoustic Matching Member)

The computer 150 acquires sound speed information about the object 100 and sound speed information about the acoustic matching member 190. In the present exemplary embodiment, the sound speed information includes the propagation velocity (sound speed) of the acoustic wave and any parameter that can be used to estimate the sound speed. For example, the sound speed can be obtained based on density $\rho$ and bulk modulus K. Therefore, in the present process, the computer 150 can acquire the density $\rho$ and the bulk modulus K beforehand, as the sound speed information, and can estimate the sound speed based on the acquired parameters.

Alternatively, in acquiring the sound speed information, the computer 150 can read the sound speed information stored in the storage unit beforehand. Further, in acquiring the sound speed information, the computer 150 can refer to a relational expression or a relation table that prescribes temperature influencing the sound speed in relation to the sound speed information, which is stored in the storage unit beforehand. In this case, the computer 150 can check the temperature of the object 100 or the acoustic matching member 190 measured by a temperature measurement unit beforehand and can acquire the sound speed information corresponding to the measured temperature with reference to the relational expression or the relation table.

Further, the computer 150 can set provisional positional information about a boundary between the object 100 and the acoustic matching member 190, and can acquire sound speeds in the object 100 and the acoustic matching member 190, as sound speed information, using the provisional positional information, which can be obtained according to a conventionally known method.

(Step S120: Process for Acquiring Positional Information about Boundary Between Object and Acoustic Matching Member)

The computer 150 acquires positional information about the boundary between the object 100 and the acoustic matching member 190. As mentioned above, the acoustic matching member 190 stored in the support member 132 is deformable. Therefore, the acoustic matching member 190 deforms when the object 100 presses the acoustic matching member 190. The boundary between the object 100 and the acoustic matching member 190 is variable in each measurement. The positional information about the boundary includes coordinate data indicating the position of the boundary and a mathematical function expressing the shape of the boundary. It is feasible to estimate the positional information about the boundary based on the positional information about the acoustic matching member. Therefore, it can be regarded that the acquisition of the positional information about the boundary completes when the acquisition of the positional information about the acoustic matching member completes.

For example, first, the computer 150 generates object information by performing conventionally known image reconstruction processing based on the signal data stored in the storage unit and an average sound speed value of an appropriately set provisional propagation path. The object information obtained in this case is, for example, initial sound pressure distribution, light energy absorption density distribution, or relative absorption coefficient distribution derived from the above-mentioned distribution. Usually, there is a significant difference between the object 100 and the acoustic matching member 190 in Gruneisen coefficient or optical absorption coefficient. Therefore, generation of photoacoustic waves from the surface of the object 100 can be recognized. In particular, in a case where the object 100 is a living organism, the generation of photoacoustic waves occurs from a blood vessel positioned adjacently to the skin surface or from a skin including a greater amount of melanin. The probe 130 can receive the photoacoustic waves generated from the surface or its vicinity together with photoacoustic waves generated from a light absorption member (e.g., a blood vessel) in the object. Therefore, the signal data includes both of the above-mentioned photoacoustic waves. More specifically, if the computer 150 performs image reconstruction processing on the signal data, the surface shape of the object 100 can be imaged based on signal data originated from photoacoustic waves generated from the surface or its vicinity. The computer 150 can obtain the positional information about the boundary between the object 100 and the acoustic matching member 190 based on the obtained image data. As a practical example, the computer 150 causes the display unit 160 to display the reconstructed image data to enable a user to mark a position corresponding to the boundary (e.g., the surface of the object 100) via the input unit 170 while confirming the displayed image. Subsequently, the computer 150 calculates coordinate values of the feature point (i.e., the marked point) designated through the input unit 170 and obtains a mathematical function that expresses the shape of the boundary through mathematical interpolation of the calculated coordinate values. Further, the computer 150 generates voxel data that expresses a three-dimensional shape of the boundary by using the mathematical function expressing the shape of the boundary, in which "1" represents the inside of the boundary (i.e., the inside of the object) and "0" represents the rest.

Although the user has designated the position that is assumed to be the boundary on the image by using the input unit 170, the computer 150 can be configured to automatically generate the positional information about the boundary through image processing on image data, instead of requiring the user to extract the feature point. Any other processing capable of acquiring positional information about a boundary from image data is employable. According to the above-mentioned method, the computer 150 can acquire the positional information about the boundary based on the measured signal data.

On the other hand, there is another method employable to acquire the positional information about the boundary. For example, it is feasible for the computer 150 to acquire the positional information about the boundary based on information obtained by another measuring apparatus (modality apparatus). Specifically, a medical modality (e.g., three-dimensional ultrasonic wave imaging apparatus, MRI, or X-ray CT) that can confirm an object included in an image is comparable to the photoacoustic apparatus. Therefore, the computer 150 can acquire the positional information about the boundary based on image data obtained by another measuring apparatus (modality apparatus) according to the above-mentioned method. In this case, to minimize a positional deviation between the image data obtained by the photoacoustic apparatus and the image data obtained by another measuring apparatus, it is desired to perform the measurement by the photoacoustic apparatus and the measurement by another measuring apparatus in similar holding states. To this end, the photoacoustic apparatus or another measuring apparatus can include a notification unit configured to notify the degree of a difference in the holding state with sounds and images. Further, the computer 150 can correct the positional deviation between the image data beforehand and subsequently acquire the positional information about the boundary based on the image data obtained by another measuring apparatus.

Further, as another method, the computer 150 can acquire a measurement result from an already known shape measuring apparatus (e.g., a stereo camera system performing a three-dimensional measurement or a shape measuring apparatus using measuring light) capable of measuring the position of the boundary. For example, one camera can be located on the lower side of the object 100 and four cameras can be located on the back, front, right, and left sides of the object 100 to acquire still images of the object 100 before starting the measurement. The computer 150 can reconstruct a three-dimensional shape of the object 100 based on the above-mentioned five still images, through conventionally known image processing and acquires the reconstructed shape as the positional information about the boundary. In this case, it is desired to perform the measurement by the photoacoustic apparatus and the measurement by the shape measuring apparatus in similar holding states. To this end, the photoacoustic apparatus or the shape measuring apparatus can include a notification unit configured to notify the degree of a difference in the holding state with sounds and images.

(Step S130: Process for Acquiring Propagation Time Information Based on Positional Information about Boundary, Sound Speed Information about Object, and Sound Speed Information about Acoustic Matching Member)

The computer 150 acquires propagation time information about the photoacoustic wave based on the positional information about the boundary acquired in step S120 and the sound speed information about the object and the sound speed information about the acoustic matching member acquired in step S110. The computer 150 acquires information about propagation time (first propagation time) t1 along an acoustic ray when the acoustic wave generated at the interesting position 101 propagates in the object 100, based on the sound speed information about the object 100. Further, the computer 150 acquires information about propagation time (second propagation time) t2 along an acoustic ray when the acoustic wave generated at the interesting position 101 propagates in the acoustic matching member, based on the sound speed information about the object 100.

In the following description, a voxel or a pixel that becomes a reconstruction target in step S140 will be described as the interesting position 101.

Hereinafter, an exemplary method for acquiring the propagation time information about the acoustic wave will be described with reference to FIGS. 4A to 4E.

Figure 4A:
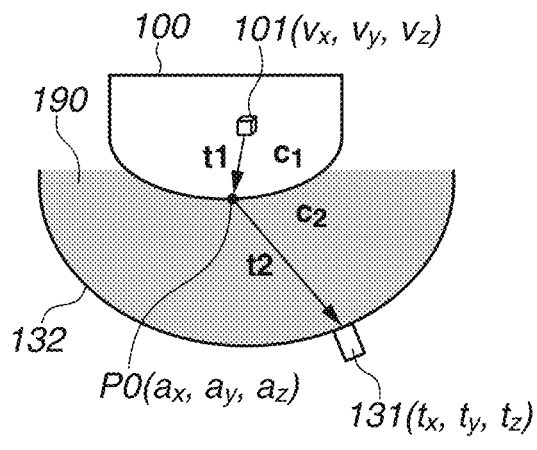
FIGS. 4A, 4B, 4C, 4D, and 4E illustrate a propagation time calculation method according to the first exemplary embodiment.
Figure 5:
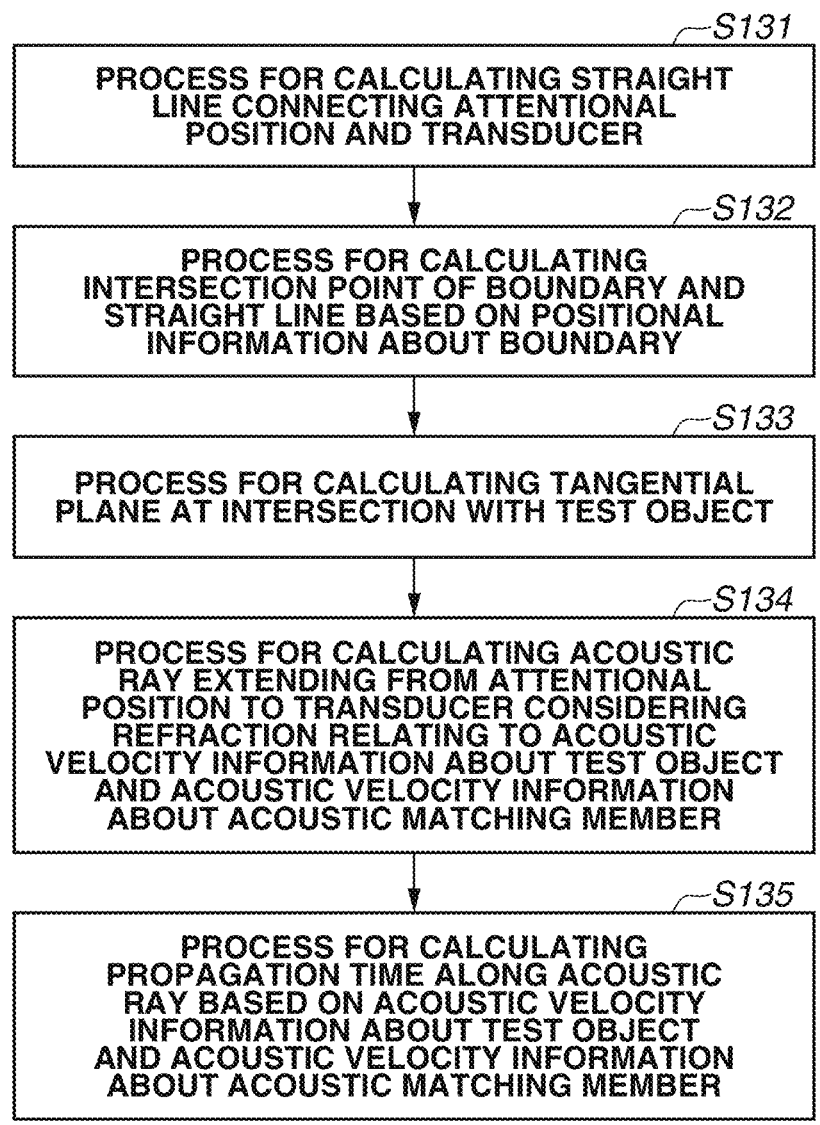
FIG. 5 is a flowchart illustrating propagation time calculation processing according to the first exemplary embodiment.

(1) Acquisition of Propagation Time Information in which Refraction is Taken into Consideration An exemplary acquisition of the propagation time information considering the refraction at the boundary will be described in detail below with reference to a processing flow illustrated in FIG. 5. The computer 150 calculates the propagation time t1 from the interesting position 101 to a refraction point P0 and the propagation time t2 from the refraction point P0 to the transducer 131, as illustrated in FIG. 4A.

(Step S131: Process for Calculating Straight Line Connecting Interesting Position and Transducer)

Figure 4D:
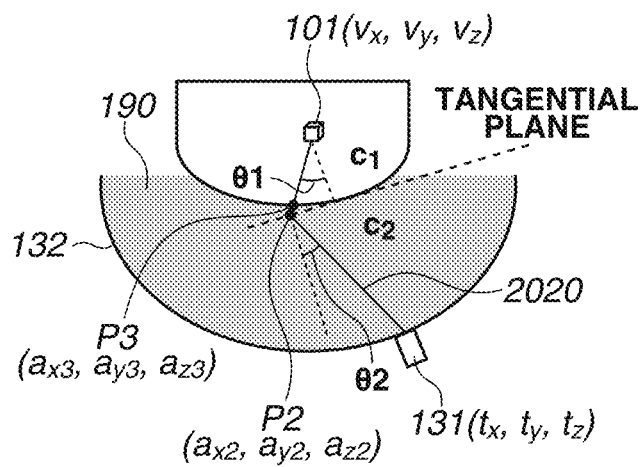
Figure 4B:
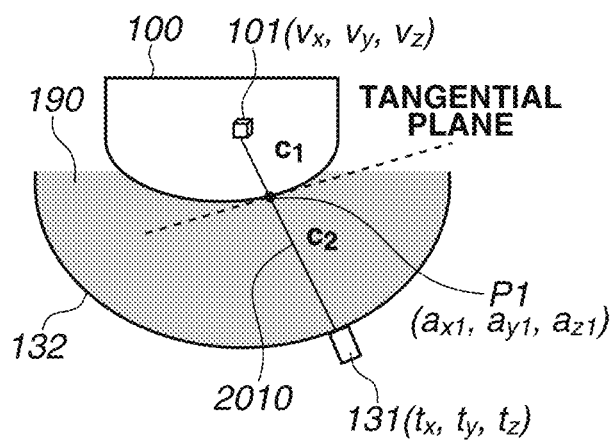

First, the computer 150 calculates a straight line connecting the interesting position 101 and the transducer 131, as illustrated in FIG. 4B. Specifically, the computer 150 obtains a first acoustic ray 2010 that can be defined by a formula of a straight line that passes a coordinate point (Vx, Vy, Vz) of the already known interesting position 101 and a coordinate point (tx, ty, tz) of the transducer 131. When d=(l, m, n) represents a direction vector, l=(tx−vx), m=(ty−vy), and n=(tz−vz) and the final formula of the straight line can be obtained in the following manner.

$$x-vx/l=y-vy/m=z-vz/n \tag{1}$$

(Step S132: Process for Calculating Intersection Point of Boundary and Straight Line Based on Positional Information about Boundary)

Next, the computer 150 calculates coordinate values (ax1, ay1, az1) of a position (i.e., intersection point P1) at which the straight line calculated in step S131 meets the boundary represented by the positional information about the boundary acquired in step S120. For example, when the positional information about the boundary is a mathematical function representing the shape of the boundary, the computer 150 can obtain the intersection point based on the formula expressing the straight line and the mathematical function representing the shape of the boundary.

(Step S133: Process for Calculating Tangential Plane at Intersection with Object)

Figure 4E:
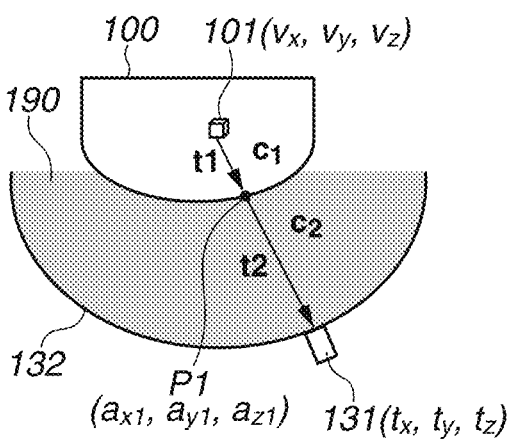
Figure 4C:
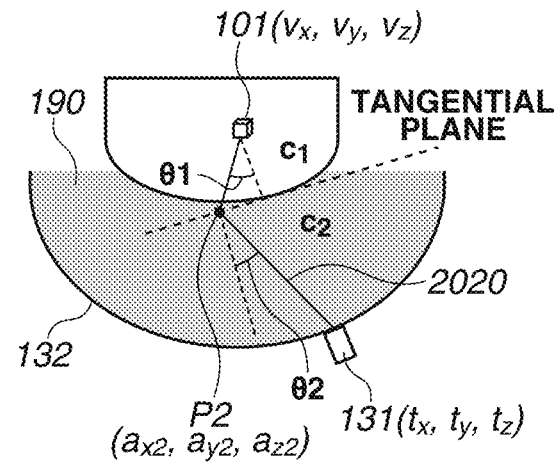

Next, the computer 150 calculates a tangential plane of the object 100 that meets the intersection point P1, as illustrated in FIG. 4C. For example, when n=(a, b, c) represents a normal vector of the tangential plane, the tangential plane can be expressed by the following formula.

$$a(x-ax1)+b(y-ay1)+c(z-az1)=0 \tag{2}$$

(Step S134: Process for Calculating Acoustic Ray Extending from Interesting Position to Transducer Considering Refraction Relating to Sound Speed Information about Object and Sound Speed Information about Acoustic Matching Member)

Next, the computer 150 calculates a second acoustic ray 2020 with respect to the tangential plane calculated in step S133, in which a refraction relating to the Snell's law is taken into consideration, as illustrated in FIG. 4C. The computer 150 obtains the second acoustic ray 2020 in such a way as to consider the refraction based on the coordinate values (Vx, Vy, Vz) of the interesting position 101 and the coordinate values (tx, ty, tz) of the transducer 131, according to the Snell's law defined by the following equation.

$$c1/c2=\sin\theta1/\sin\theta2 \tag{3}$$

Next, the computer 150 calculates coordinate values (ax2, ay2, az2) of an intersection point P2 of the second acoustic ray 2020 and the tangential plane, as illustrated in FIG. 4C. Further, the computer 150 calculates coordinate values (ax3, ay3, az3) of an intersection point P3 of the second acoustic ray 2020 and the boundary, as illustrated in FIG. 4D.

Next, the computer 150 evaluates a distance between the intersection point P2 and the intersection point P3 and determines whether the evaluated distance is within a predetermined numerical value range. If it is determined that the distance is within the predetermined numerical value range, the computer 150 acquires the evaluated line as an acoustic ray extending from the interesting position 101 to the transducer 131. On the other hand, if it is determined that the distance is not included in the predetermined numerical value range, the computer 150 calculates a tangential plane of the object 100 that meets the intersection point P3 in the same manner as described in step S133. Then, the computer 150 performs the processing of step S134 based on the obtained tangential plane passing through the intersection point P3. The computer 150 repeats the processing of steps S133 and S134 until it is determined that the distance is within the predetermined numerical value range. More specifically, the computer 150 calculates the acoustic ray through optimization processing for minimizing the distance between the intersection point of the tangential plane and the acoustic ray and the intersection point of the boundary and the acoustic ray. The minimum value can be obtained when a calculated error is included in a predetermined numerical value range.

In the present exemplary embodiment, the method for calculating the acoustic ray using the distance between the intersection point of the tangential plane and the acoustic ray and the intersection point of the boundary and the acoustic ray as an evaluation value has been described. However, any other method capable of acquiring an acoustic ray while considering the refraction relating to the sound speed information about the object and the sound speed information about the acoustic matching member is employable.

(Step S135: Process for Calculating Propagation Time Along Acoustic Ray Based on Sound Speed Information about Object and Sound Speed Information about Acoustic Matching Member)

The computer 150 calculates propagation time along the acoustic ray acquired in step S134 that extends from the interesting position 101 to the transducer 131. The computer 150 calculates a propagation distance d1 between the interesting position 101 and an intersection point of the acoustic ray and the boundary and calculates propagation time t1 (=d1/c1) by dividing the propagation distance d1 by sound speed c1 in the object 100. Further, the computer 150 calculates a propagation distance d2 from the intersection point of the acoustic ray and the boundary to the transducer 131 and calculates propagation time t2 (=d2/c2) by dividing the propagation distance d2 by sound speed c2 in the acoustic matching member 190. Then, the computer 150 acquires the time (t1+t2) as the propagation time of the acoustic wave traveling from the interesting position 101 to the transducer 131.

The computer 150 can calculate the propagation distance d1 and the propagation distance d2 according to the following formulas.

$$d1=\text{sqrt}[(vx-ax)^2+(vy-ay)^2+(vz-az)^2] \quad (4)$$

$$d2=\text{sqrt}[(tx-ax)^2+(ty-ay)^2+(tz-az)^2] \quad (5)$$

In this case, the computer 150 uses coordinate values (ax, ay, az) of the intersection point of the acoustic ray and the boundary calculated in step S134, coordinate values (Vx, Vy, Vz) of the interesting position 101, and coordinate values (tx, ty, tz) of the transducer 131.

(2) Acquisition of Propagation Time Information in which No Refraction is Taken into Consideration The computer 150 can acquire propagation time information about the path extending from the interesting position 101 to the transducer 131, without considering the refraction at the boundary between the object 100 and the acoustic matching member 190. More specifically, as illustrated in FIG. 4E, the computer 150 can be configured to calculate coordinate values (ax1, ay1, az1) of the intersection point P1 at which the straight line connecting the interesting position 101 to the transducer 131 meets the boundary and can calculate the propagation time t according to the following formulae.

$$d1=\text{sqrt}[(vx-ax1)^2+(vy-ay1)^2+(vz-az1)^2] \quad (6)$$

$$d2=\text{sqrt}[(tx-ax1)^2+(ty-ay1)^2+(tz-az1)^2] \quad (7)$$

$$t=d1/c1+d2/c2 \quad (8)$$

The above-mentioned approximation can be established when the ratio of sound speed c1 in the object 100 to sound speed c2 in the acoustic matching member 190 is sufficiently small. Therefore, the computer 150 can acquire the propagation time information using the above-mentioned method in which no refraction is taken into consideration when the ratio of the sound speed c1 in the object 100 to the sound speed c2 in the acoustic matching member 190 is within a predetermined numerical value range (e.g., equal to or less than a threshold value), referring the information acquired in step S110. Further, the computer 150 can acquire the propagation time information using the above-mentioned method in which refraction is taken into consideration when the ratio of the sound speed c1 in the object 100 to the sound speed c2 in the acoustic matching member 190 is out of the predetermined numerical value range (e.g., greater than the threshold value), referring the information acquired in step S110. Further, if the sound speed c2 in the acoustic matching member 190 is already known, the computer 150 can acquire the propagation time information according to the method considering no refraction when the sound speed c1 in the object 100 acquired in step S110 is within the predetermined numerical value range. Further, the computer 150 can acquire the propagation time information according to the method considering refraction when the sound speed c1 in the object 100 acquired in step S110 is out of the predetermined numerical value range.

In a case where there is a plurality of interesting positions, the computer 150 can acquire the propagation time information according to the above-mentioned method for each interesting position. Further, the computer 150 can calculate propagation times for a limited number of interesting positions according to the above-mentioned method and then acquire propagation time information about the remaining interesting positions by interpolating the calculated propagation times. Further, the computer 150 can be configured to calculate a propagation time for a specific interesting position according to the above-mentioned method and allocate the calculated propagation time to peripheral interesting positions. More specifically, the computer 150 can allocate a propagation time acquired for a specific minimum unit to the remaining minimum units.

(Step S140: Process for Acquiring Object Information Based on Propagation Time Information)

The computer 150 acquires object information based on the propagation time information acquired in step S130 and signal data stored in the storage unit.

For example, in the present process, Universal back-projection (UBP) method that can be expressed by the following formula (9) is usable as an initial sound pressure calculation method.

$$p_0(r_0) = \frac{\sum_i^N b\left(r_i, t = \frac{|r_i - r_0|}{c}\right) \cdot \Delta\Omega_i}{\sum_i^N \Delta\Omega_i} \quad (9)$$

$$b(r, t) = 2p(r, t) - 2t\frac{\partial p(r, t)}{\partial t}$$

In the above-mentioned formula, $r_0$ represents a position vector indicating a voxel or a pixel (i.e., an interesting position) to be imaged, $p_0(r_0, t)$ represents initial sound pressure of the interesting position to be imaged, and c represents sound speed of the propagation path. Further, $\Delta\Omega_i$ represents a solid angle of the i-th transducer 131 viewed from the position to be imaged, and N represents the number of the transducers 131 used in the imaging. The formula (9) indicates phase phasing and adding processing (i.e., reverse projection) including performing differential or comparable processing on a received signal p ($r_i$, t) and multiplying the processed signal with a weighted value of solid angles.

In the formula (9), "t" represents a propagation time, i.e., a time required for the photoacoustic wave to propagate an acoustic ray connecting the interesting position and the transducer 131. More specifically, the propagation time "t" is the propagation time acquired in step S130.

Further, b ($r_i$, t) can be calculated through additional arithmetic processing, such as frequency filtering (e.g., low-pass, high-pass, or band-pass), deconvolution, envelope demodulation, or wavelet filtering. Further, in the present invention, any other reconstruction algorithm is employable if it is a method capable of realizing the reconstruction by obtaining the propagation time of the acoustic ray connecting the transducer and the interesting position. For example, Filtered back-projection, Model based Reconstruction (Iterative Reconstruction) is employable as the time domain reverse projection method.

The computer 150 can acquire optical fluence distribution information about light in the object 100, when the light is emitted to the object 100, using the positional information about the boundary obtained in step S120. In this case, the computer 150 can calculate a profile (i.e., a source) of light at the surface of the object 100 based on the positional information about the boundary obtained in step S120. Further, the computer 150 can set a boundary condition in the light propagation calculation using the positional information about the boundary obtained in step S120. Further, the computer 150 can acquire optical absorption coefficient distribution information using initial sound pressure distribution information and the optical fluence distribution information. Further, the computer 150 can acquire density distribution information, such as degree of oxygen saturation distribution, using the optical absorption coefficient distribution information. For example, the computer 150 can acquire the density distribution based on an optical absorption coefficient distribution of a plurality of beams having different wavelengths. The computer 150 outputs to the display unit 160 the object information (e.g., initial sound pressure distribution, optical absorption coefficient distribution, or density distribution) obtained in the present process.

(Step S150: Process for Displaying Object Information)

In the present process, the computer 150 causes the display unit 160 to display the object information based on the object information acquired in step S140. The object information that can be displayed in this case includes the initial sound pressure distribution, the optical absorption coefficient distribution, and the density distribution (i.e., the degree of oxygen saturation distribution).

As mentioned above, the information acquisition method according to the present exemplary embodiment can prevent the accuracy of object information from deteriorating due to a difference in propagation time that may be caused by the deformable acoustic matching member.

In a second exemplary embodiment, a method capable of accurately acquiring positional information about a boundary based on object information will be described. More specifically, the method according to the present exemplary embodiment includes obtaining object information using positional information about a boundary between an object and an acoustic matching member and newly acquiring positional information about the boundary based on the obtained object information. The method further includes acquiring object information again based on the updated positional information about the boundary, as described in detail below. The present exemplary embodiment will be described below with reference to the photoacoustic apparatus illustrated in FIG. 1 and a processing flow illustrated in FIG. 6. Constituent components similar to those already described in the first exemplary embodiment are denoted by the same reference numerals, and descriptions thereof are omitted.

Hereinafter, signal processing that can be performed by the computer 150 will be described in detail below with reference to the processing flow illustrated in FIG. 6. The computer 150 starts the processing illustrated in FIG. 6 after completing storing signal data originated from an electric signal output from the probe 130 in the storage unit thereof.

(Step S210: Process for Acquiring Provisional Sound Speed Information about Propagation Path)

The computer 150 acquires provisional sound speed information about a propagation path of an acoustic wave generated at the interesting position. In this case, the computer 150 can regard single sound speed information as the provisional sound speed information under the assumption that the propagation path is a uniform medium. Further, the computer 150 can provisionally set sound speed information about the object 100 and sound speed information about the acoustic matching member 190, respectively, as the provisional sound speed information about the propagation path.

In acquiring the provisional sound speed information, the computer 150 can read the sound speed information stored in the storage unit beforehand. Further, the computer 150 can be configured to acquire the sound speed information about the acoustic matching member 190 by reading the sound speed information from the storage unit and acquire the provisional sound speed information about the object 100 based on signal data. More specifically, the computer 150 sets provisional positional information about the boundary between the object 100 and the acoustic matching member 190. Then, the computer 150 acquires the sound speed information about the object 100 by analyzing the signal data or the object information obtainable from the signal data using the provisionally set positional information about the boundary and the sound speed information about the acoustic matching member 190 by using the sound speed information about the object 100 as a variable.
(Step S220: Process for Acquiring First Object Information Based on Provisional Sound Speed Information)

The computer 150 acquires first object information based on the provisional sound speed information acquired in step S210 and the signal data stored in the storage unit. In acquiring the object information, the processing of steps S120 to S140 is usable. In this case, the positional information about the boundary between the object 100 and the acoustic matching member 190 is provisional information. The provisional positional information about the boundary can be entered by a user via the input unit 170 or can be acquired from the storage unit that stores the positional information beforehand. However, in a case where the medium is assumed to be uniform in quality in step S210, the computer 150 can acquire the object information without setting the provisional positional information about the boundary.
(Step S230: Process for Acquiring Positional Information about Boundary Based on First Object Information)

The computer 150 acquires the positional information about the boundary based on the first object information acquired in step S220. In acquiring the positional information about the boundary based on the object information, the method described in step S120 is applicable to the first object information.

The present process acquires the positional information about the boundary based on the object information. Therefore, the positional information about the boundary can be accurately acquired, compared to the positional information about the boundary provisionally set in step S210.
(Step S240: Process for Acquiring Sound Speed Information about Acoustic Matching Member)

The computer 150 acquires sound speed information about the acoustic matching member 190. In acquiring the sound speed information about the acoustic matching member 190, the computer 150 can read the sound speed information about the acoustic matching member 190 stored in the storage unit beforehand. Further, in acquiring the sound speed information about the acoustic matching member 190, the computer 150 can refer to a relational expression or a relation table that prescribes temperature influencing the sound speed information about the acoustic matching member 190 in relation to the sound speed information, which is stored in the storage unit beforehand. In this case, the computer 150 can check the temperature of the acoustic matching member 190 measured by the temperature measurement unit beforehand and can acquire the sound speed information corresponding to the measured temperature with reference to the relational expression or the relation table.
(Step S250: Process for Acquiring Sound Speed Information about Object Based on Positional Information about Boundary and Sound Speed Information about Acoustic Matching Member)

The computer 150 acquires sound speed information about the object 100 based on the positional information about the boundary acquired in step S230, the sound speed information about the acoustic matching member 190 acquired in step S240, and the signal data stored in the storage unit. First, the computer 150 provisionally sets the sound speed information about the object 100. Next, the computer 150 acquires propagation time information about the acoustic wave traveling from the interesting position to the transducer 131 as described in step S130, using the provisionally determined sound speed information about the object 100, the positional information about the boundary, and the sound speed information about the acoustic matching member 190. Next, the computer 150 acquires optimum sound speed information about the object 100 by analyzing signal data corresponding to the acquired propagation time information or object information obtainable from the signal data. In acquiring the optimum sound speed information, a conventionally known method is employable. As a modified example, the computer 150 can be configure to acquire optimum sound speed information in the present process, by using the sound speed information about the acoustic matching member 190 as a variable in addition to the sound speed information about the object 100, without performing the processing in step S240.

As mentioned above, the positional information about the boundary used in the present process is excellent in accuracy compared to the positional information about the boundary provisionally set in step S210. Therefore, the sound speed information about the object 100 acquired in the present process is excellent in accuracy compared to the sound speed information provisionally set in step S210.
(Step S260: Process for Calculating Propagation Time Based on Positional Information about Boundary, Sound Speed Information about Acoustic Matching Member, and Sound Speed Information about Object)

The computer 150 acquires the propagation time information about the acoustic wave that travels from the interesting position to the transducer 131 using the positional information about the boundary acquired in step S230, the sound speed information about the acoustic matching member 190 acquired in step S240, and the sound speed information about the object 100 acquired in step S250. In the present process, the method described in step S130 is usable in acquiring the propagation time information.
(Step S270: Process for Acquiring N-Th Object Information Based on Propagation Time Information)

The computer 150 acquires second object information using the propagation time information acquired in step S260 and the signal data stored in the storage unit. In the present process, the computer 150 can acquire the object information according to the method described in step S140. The computer 150 designates the object information obtained in step S220 as first object information and designates the object information obtained in the present process as n-th object information (n is an integer equal to or greater than 2). The computer 150 designates the object information initially acquired in the present process as second object information and designates the object information acquired in the (n−1)th process as n-th object information.

Then, if it is determined that m-th object information has not been acquired in the present process (NO in step S280), the operation proceeds to step S290. If it is determined that the m-th object information has been acquired (YES in step S280), the operation proceeds to step S300.

Step S290: Process for Acquiring and Updating Positional Information about Boundary Based on N-Th Object Information)

The computer 150 acquires the positional information about the boundary again based on the n-th object information acquired in step S270 and updates the positional information about the boundary in the storage unit. Alternatively, the computer 150 can additionally store newly obtained positional information about the boundary, instead of overwriting the data in the storage unit. In this case, it can be regarded that the positional information about the boundary has been updated. In acquiring the positional information about the boundary based on the object information, the method described in step S120 can be applied to the n-th object information.

In acquiring the n-th object information acquired in step S270, the sound speed information about the object 100 accurately acquired in step S250 is taken into consideration. Therefore, the acquired information is excellent in accuracy compared to the first object information acquired in step S220. Therefore, the positional information about the boundary obtained in the present process is excellent in accuracy compared to the positional information about the boundary obtained in step S230.

Therefore, various kinds of information obtained in steps S250 through S270 in the second and subsequent processes is excellent in accuracy compared to various kinds of information obtained in the initial process. As a result, the m-th object information displayed in step S300 is excellent in accuracy compared to the first object information.

According to the present exemplary embodiment described above, the computer 150 terminates the calculation processing upon completing the acquisition of the m-th object information. The number of repetitions in calculation can be set beforehand. Alternatively, each user can input the number of repetitions via the input unit 170. Further, the computer 150 can be configured to perform image analysis on the n-th object information and terminate the calculation processing if the image analysis result indicates that an image quality related parameter is within a predetermined numerical value range. Through the above-mentioned processing, it is feasible to continue the calculation processing until a desired image quality can be obtained. Further, because the calculation processing terminates when the desired image quality has been obtained, it is feasible to prevent the calculation processing from being repeated redundantly.

The information acquisition apparatuses described in the first and second exemplary embodiments acquire object information originated from the photoacoustic wave generated due to photoacoustic effects. However, the present invention can be realized by any other method capable of acquiring object information by using acoustic waves. The present invention is also applicable to an ultrasonic wave imaging apparatus capable of acquiring object information with a probe, which is operable as an ultrasonic irradiation unit and a receiving unit, configured to transmit and receive ultrasonic waves. In this case, as described in the first or second exemplary embodiment, it is feasible to employ a method for preventing the accuracy in acquisition of the object information from deteriorating due to a deformable acoustic matching member. The object information acquired in this case by the ultrasonic wave imaging apparatus includes B-mode images, Doppler images, and elastography images.

An example of the photoacoustic apparatus according to the present exemplary embodiment will be described in detail below. A first exemplary photoacoustic apparatus will be described with reference to the schematic apparatus illustrated in FIG. 1. The first exemplary photoacoustic apparatus includes a second-order harmonic YAG laser exciting Ti: sa laser system, as the light source 111. The Ti: sa laser can irradiate the object 100 with the pulsed light 113 having the wavelength in the range from 700 nm to 900 nm. The optical system 112 (including a mirror and a beam expander) widens a laser beam to have a radius of approximately 3 cm before the laser beam is emitted to an object surface. The probe 130 employed in the present exemplary embodiment includes 512-ch piezoelectric transducers 131 arranged spirally on the semi-spherical support member 132. The semi-spherical support member 132 serves as a container that holds the acoustic matching member 190 (e.g., water) intervening between the object 100 and the transducers 131. Further, the signal data collection unit 120 can simultaneously receive all of 512-ch data from the probe 130. The signal data collection unit 120 amplifies received analog data and converts the amplified analog data into digital data. Further, the signal data collection unit 120 transfers the converted data to the computer 150. The sampling frequency and the sampling number of the signal data collection unit 120 are 40 MHz and 4096, respectively. The receiving start time is illumination timing of light. The object 100 is a phantom that simulates a living organism. The object 100 is made of an urethan rubber that contains titanium oxide, serving as a scatterer, and ink, serving as an absorber. The object 100 has a semi-spherical shape. Further, a wire or a ring serving as the light absorption member 103 is embedded in the semi-spherical urethan phantom. Further, a surface of the phantom is covered with a sheet that simulates a skin. The cover sheet has an optical absorption coefficient that is greater than that of the phantom. The urethan phantom is acoustically in contact with the transducers 131 via the water (i.e., the acoustic matching member 190). The water freely deforms along the shape of the phantom. The average sound speed ($c_b$) of the urethan phantom is 1409 m/s, and the sound speed ($c_a$) of the water (i.e., the acoustic matching member) is 1509 m/s. The sound speeds are different from each other. First, the Ti: sa laser irradiates the phantom with light having the wavelength of 755 nm. The signal obtained in this case is stored in the storage unit of the computer 150.

Figure 7A:
FIGS. 7A and 7B illustrate images of object information obtained in a comparable example or in the first exemplary embodiment.

Next, the computer 150 performs image reconstruction processing using the above-mentioned signal data. In this case, the method used for the image reconstruction is time domain UBP method. Further, the sound speed used in this case is 1509 m/s, which is the average sound speed of water. More specifically, in performing the image reconstruction processing, the computer 150 calculates the propagation time under the assumption that the entire propagation path of the acoustic wave is completely the water (i.e., the acoustic matching member). FIG. 7A illustrates an example of a reconstructed image obtained in this case. The example illustrated in FIG. 7A can be regarded as an image of object information obtained from a comparable example.

Next, the computer 150 acquires shape information about the phantom using the reconstructed image illustrated in FIG. 7A. Although not illustrated in FIG. 7A, it is feasible to confirm a surface shape of the phantom based on photoacoustic waves generated from the urethan phantom surface. The computer 150 extracts the surface shape of the phantom through image processing according to preliminarily programmed software. A method employed in the present exemplary embodiment includes enabling a user to designate a position that probably coincides with the surface on the GUI and calculating a mathematical function capable of approximating a boundary shape by spline interpolating coordinate values of the designated position. Subsequently, the computer 150 stores in the storage unit thereof the obtained mathematical function as positional information about the boundary between the object 100 and the acoustic matching member 190.

Figure 7B:
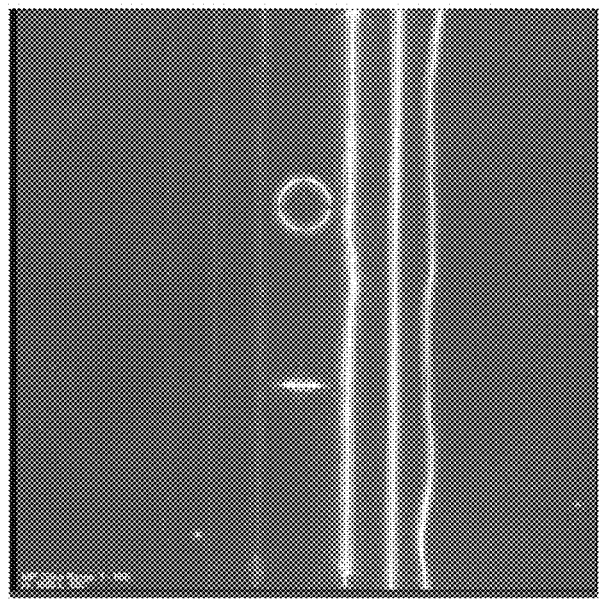

Next, the computer 150 generates an initial sound pressure distribution by using the mathematical function that approximates the boundary shape. In this case, the computer 150 calculates an intersection point of an acoustic ray considering the refraction due to the difference in sound speed, for all voxels at the interesting position in the phantom, based on the mathematical function that approximate the boundary shape and the coordinate values of the transducer 131. Then, the computer 150 obtains the propagation distance d1 of the acoustic ray in the phantom and the propagation distance d2 of the acoustic ray in the water based on the coordinate values of the intersection point. Further, the computer 150 calculates the propagation time of each acoustic ray using the obtained propagation distances d1 and d2, the average sound speed c1 (i.e., 1409 m/s) of the phantom, and the sound speed c2 (i.e., 1509 m/s) of the water. The computer 150 calculates the initial sound pressure distribution based on the propagation time of each acoustic ray, through image reconstruction processing. In the present exemplary embodiment, the method used for the image reconstruction is the UBP method. FIG. 7B illustrates an example of the reconstructed image obtained in this case.

Both of the examples illustrated in FIGS. 7A and 7B include a ring-shaped light absorption member and a wire-shaped light absorption member disposed in the urethan phantom. As apparent from a comparison between two examples, the reconstructed image illustrated in FIG. 7A is blurred entirely because of lowness in contrast. More specifically, the reconstructed image of FIG. 7A is inferior to the reconstructed image of FIG. 7B in resolution and image contrast. According to the reconstructed image of FIG. 7B, images of the light absorption members can be confirmed vividly and the entire image is clear. As mentioned above, in a case where an acoustic matching member is present between an object and a probe and the acoustic matching member is deformable along the shape of the object, the information acquisition method according to the present exemplary embodiment can obtain satisfactory image data while preventing the resolution from deteriorating due to difference in sound speed between the acoustic matching member and the object.

Figure 8:
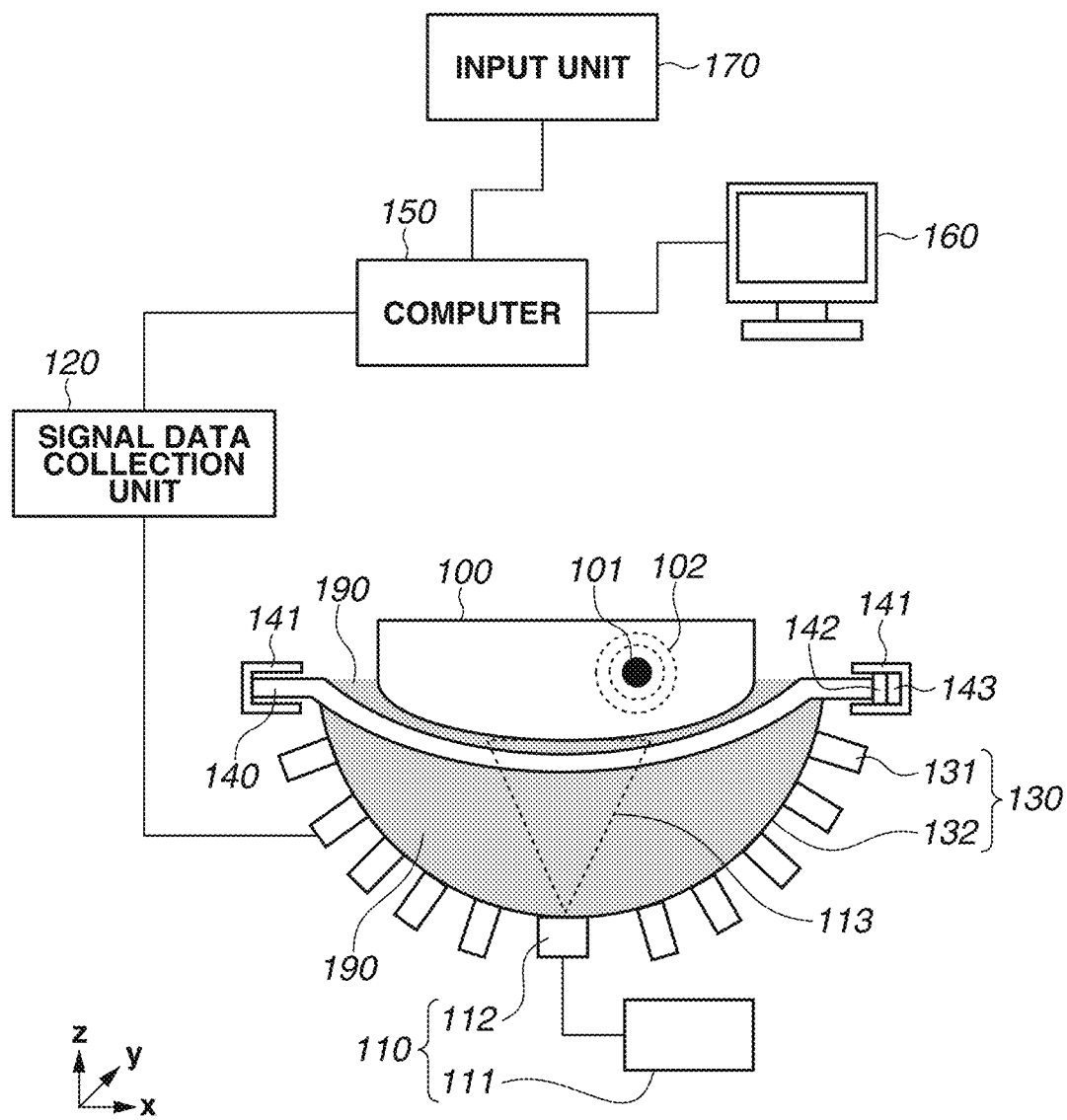
FIG. 8 schematically illustrates a photoacoustic apparatus according to the second exemplary embodiment.

A second exemplary photoacoustic apparatus according to the present exemplary embodiment will be described in detail below with reference to FIG. 8. The second exemplary photoacoustic apparatus includes an alexandrite laser (i.e., a solid-state laser) capable of generating the light of 755 nm as the light source 111. The phantom is an urethan phantom that simulates the shape of a breast. Similar to the first exemplary embodiment, the phantom includes a light absorption member embedded therein. Similar to the first exemplary embodiment, the probe 130 according to the present exemplary embodiment includes a total of 512 transducers 131 arranged spirally on a semi-spherical surface. The semi-spherical probe 130 holds the acoustic matching member 190 (e.g., water). The phantom is acoustically in contact with the transducers 131 via the water. Further, to hold the urethan phantom (i.e., the object 100), the photoacoustic apparatus includes a plastic cup 140 having a thickness of approximately 0.5 mm. In other words, the plastic cup 140 serves as a holding unit. The plastic cup is basically semi-spherical. On the other hand, the shape of the phantom is complicated because the phantom simulates the shape of a breast. Therefore, the internal space of the plastic cup 140 is filled with the acoustic matching member 190 (i.e., water) for the acoustic matching between the phantom 100 and the transducers 131. The water (i.e., liquid serving as the acoustic matching member 190) freely deforms along the shape of the phantom.

The holding cup (i.e., the holding unit) can hold the object 100 during the measurement of the shape of the object 100. The holding cup prevents the object 100 from moving so that the object 100 is positioned securely in the holding cup. Although the holding cup employed in the present exemplary embodiment is the plastic cup 140, any other appropriate holding cup is usable. For example, the holding cup can be made of appropriate resin material, such as polycarbonate, polyethylene, or polyethylene terephthalate. It is desired that the holding cup is sufficiently rigid to hold the object 100. The holding cup can be made of light-transmitting material that transmits measurement light. It is desired that the impedance of the holding cup is comparable to that of the object 100. If the object 100 has a curved surface (e.g., a breast), the holding cup can be configured to have a concaved portion. In this case, the object 100 can be inserted in the concaved portion of the holding cup.

In the present exemplary embodiment, the plastic cup 140 (i.e., the holding unit) is fixed to installation portions 141. The installation portions 141 can be configured to selectively support one of a plurality of types of holding cups prepared beforehand considering various object sizes. For example, the installation portions 141 can be configured to selectively support one of a plurality of holding cups that is different in radius of curvature or in center of curvature.

Further, each holding cup can be accompanied by a tag 142 that registers specifications of the holding cup. For example, the specifications of the holding cup 140 that can be registered in the tag 142 include radius of curvature, center of curvature, sound speed information, and identification ID. A reading unit 143 can read the specifications registered in the tag 142 and transfer the acquired data to the computer 150. The reading unit 143 is located in the installation portion 141 so that the reading unit 143 can easily read the tag 142 when the holding cup is attached to the installation portion 141. For example, the tag 142 is a barcode and the reading unit 143 is a barcode reader. An inner space between the object 100 and the plastic cup 140 is filled with the acoustic matching member 190.

First, the alexandrite laser emits light having the wavelength of 755 nm. The computer 150 stores a signal obtained in this case in the storage unit thereof. Next, the computer 150 assumes that the entire plastic cup is a phantom and sets the average sound speed (i.e., 1409 m/s) of the phantom for an internal region of the plastic cup 140. Further, the computer 150 sets the sound speed (i.e., 1509 m/s) of the water for an external region of the plastic cup 140. Then, the computer 150 calculates a light energy absorption density distribution according to the sound speed having been set as mentioned above, by performing image reconstruction processing on the signal data.

Next, the computer 150 extracts positional information about the boundary between the phantom and the acoustic matching member 190 (i.e., shape information about the phantom) from the generated light energy absorption density distribution. In the present exemplary embodiment, the computer 150 uses an automatic extraction method, which includes discriminating the interior of the phantom from the exterior of the phantom through appropriate image processing (e.g., binarizing processing) and finally calculating three-dimensional voxel data in which "1" represents voxel data in the phantom and "0" represents the rest. The computer 150 performs the above-mentioned processing according to preliminarily programmed software. Subsequently, the computer 150 stores in the storage unit thereof the extracted voxel data as the positional information about the boundary.

Next, the computer 150 generates a light energy absorption density distribution based on the voxel data stored in the storage unit that expresses the boundary. A generation method usable in this case is similar to the method described in the first exemplary embodiment. The reconstructed image obtained in this case is similar to the example illustrated in FIG. 7B. The computer 150 takes a propagation delay of the acoustic wave into consideration because the plastic cup 140 may cause such a delay. The computer 150 can be configured to acquire the specifications (e.g., radius of curvature, center of curvature, sound speed information, and identification ID) of the plastic cup 140 (i.e., the holding unit) beforehand according to the above-mentioned method and acquire the propagation delay to be caused by the plastic cup 140 with reference to the obtained specifications.

Next, to convert the light energy absorption density distribution into an optical absorption coefficient distribution, the computer 150 calculates an optical fluence distribution of the light emitted to the phantom in the phantom (which may be referred to as "light quantity distribution"). The computer 150 calculates the optical fluence distribution in the phantom based on the previously obtained voxel data that expresses the boundary. Further, in obtaining the optical fluence distribution in the phantom, the computer 150 solves a light diffusion equation by using an irradiation intensity distribution of the light emitted from the alexandrite laser, and an average optical absorption coefficient and an equivalent scattering coefficient of the phantom obtained beforehand by another measuring apparatus. Subsequently, the computer 150 divides the light energy absorption density distribution by the calculated optical fluence distribution in the phantom to acquire the converted optical absorption coefficient distribution. More specifically, the computer 150 uses the positional information about the boundary between the object and the acoustic matching member not only for the image reconstruction processing on the signal data but also for the acquisition of the optical fluence distribution in object.

As mentioned above, in a case where an acoustic matching member deformable along the shape of an object is present between the object and a probe, the information acquisition method according to the present exemplary embodiment can obtain satisfactory image data while preventing the resolution from deteriorating due to difference in sound speed between the acoustic matching member and the object.

An information acquisition apparatus according to a third exemplary embodiment will be described in detail below with reference to FIG. 1. A system according to the third exemplary embodiment can realize ultrasonic wave imaging, in which each transducer 131 transmits an acoustic wave (ultrasonic wave) to the object 100 and receives a reflected wave of the transmitted ultrasonic wave or a scattering wave.

The object 100 used in the present exemplary embodiment is a semi-spherical urethan phantom similar to that in the first exemplary embodiment. The probe 130 includes 512-ch transducers 131 that can transmit acoustic waves and arranged spirally on the semi-spherical support member 132. The signal data collection unit 120 can simultaneously receive all of 512-ch data from the probe 130. The signal data collection unit 120 amplifies received analog data and converts the amplified analog data into digital data. Further, the signal data collection unit 120 transfers the converted data to the computer 150. Unlike the first exemplary embodiment, the signal data collection unit 120 according to the present exemplary embodiment is capable of transmitting an acoustic wave to the transducer of each channel.

First, the system according to the present exemplary embodiment causes a specific transducer to transmit an ultrasonic wave to the object 100 and causes the transducers 131 of all channels to receive an acoustic wave reflected or scattered from object. Subsequently, the system according to the present exemplary embodiment changes the transducer that transmits an ultrasonic wave to the object 100 and repeats the above-mentioned processing a plurality of times. The computer 150 stores in the storage unit thereof a plurality of pieces of signal data obtained through the repetitive processing. Next, the computer 150 performs image reconstruction processing on the plurality of pieces of signal data according to the software stored beforehand. The image reconstruction performed in this case is time domain reconstruction usually employed for the ultrasonic wave imaging. Compared to the photoacoustic imaging, it is necessary to consider a propagation time corresponding to a propagation distance from an acoustic wave transmission transducer to an interesting voxel. As a result, the system can obtain a three-dimensional ultrasonic wave imaging image. In general, the ultrasonic wave imaging is characterized by imaging an acoustic impedance difference in the object. In the present exemplary embodiment, there is a significant difference in acoustic impedance between the urethan phantom and the water (i.e., the acoustic matching member). Therefore, a clear boundary between the water and the urethan phantom can be recognized in the ultrasonic wave imaging image.

In the present exemplary embodiment, a reflected or scattered acoustic wave generated from an acoustic wave transmitted from a transducer serving as the ultrasonic irradiation unit is referred to as "reflected wave." Further, a signal obtainable when a transducer serving as an ultrasonic wave receiving unit receives the reflected wave is referred to as "echo signal." The ultrasonic irradiation unit and the ultrasonic wave receiving unit can be constituted as a single (or common) transducer or can be constituted as separate transducers.

Next, the computer 150 generates three-dimensional voxel data expressing a three-dimensional shape of the boundary based on the obtained three-dimensional ultrasonic wave imaging image according to a method similar to that described in the second exemplary embodiment. Subsequently, similar to other exemplary embodiments, the computer 150 generates an initial sound pressure distribution (i.e., object information about the phantom) by using the three-dimensional voxel data expressing the three-dimensional shape of the boundary.

As mentioned above, in a case where an acoustic matching member deformable along the shape of an object is present between the object and a probe, the information acquisition method according to the present exemplary embodiment can obtain satisfactory image data while preventing the image quality (e.g., resolution) from deteriorating due to difference in sound speed between the acoustic matching member and the object.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-254372, filed Dec. 25, 2015, which is hereby incorporated by reference herein in its entirety.

What is claimed is:

1. An information acquisition apparatus, comprising:
a container configured to store an acoustic matching member which is deformable;
a transducer configured to receive an acoustic wave generated from an object and output a signal; and
a memory storing a program; and
one or more processors which, by executing the program, function as:
a processing unit configured to acquire object information based on the signal,
wherein the transducer is disposed in such a way as to receive the acoustic wave having propagated in the acoustic matching member stored in the container, and
the processing unit is configured to:
acquire sound speed information in a propagation path of the acoustic wave,
acquire first positional information of a boundary between the acoustic matching member and the object,
acquire image data using the signal, the sound speed information, and the first positional information,
update the first positional information to second positional information of the boundary between the acoustic matching member and the object, based on the acquired image data, and
update the sound speed information using the signal and the second positional information.

2. The information acquisition apparatus according to claim 1, wherein the processing unit acquires image data using the signal, the updated sound speed information, and the second positional information.

3. The information acquisition apparatus according to claim 2, further comprising an optical illumination unit configured to emit light to the object,
wherein the transducer receives the acoustic wave generated from the object in response to light emission from the optical illumination unit, and wherein the processing unit acquires optical fluence distribution information of the light emitted to the object in the object using the second positional information, and
acquires information relating to optical absorption coefficient as the image data using the signal, the updated sound speed information, the second positional information, and the optical fluence distribution information.

4. The information acquisition apparatus according to claim 1, wherein the processing unit updates the first positional information based on an instruction entered via an input unit with respect to the image data.

5. The information acquisition apparatus according to claim 1, wherein the processing unit updates the first positional information by analyzing the image data.

6. An information acquisition method, comprising:
acquiring a signal originated from an acoustic wave generated from an object and traveling in an acoustic matching member which is deformable;
acquiring sound speed information about a propagation path of the acoustic wave;
acquiring first positional information of a boundary between the acoustic matching member and the object;
acquiring image data using the signal, the sound speed information, and the first positional information;
updating the first positional information to second positional information of the boundary between the acoustic matching member and the object, based on the acquired image data; and
updating the sound speed information using the signal and the second positional information.

7. A non-transitory computer-readable storage medium storing a program that causes a computer to execute the information acquisition method according to claim 6.

8. The information acquisition apparatus according to claim 1, further comprising a probe that includes a plurality of transducers and the container that supports the plurality of transducers.

9. The information acquisition apparatus according to claim 8, wherein the plurality of transducers are arranged on a flat surface or a curved surface of the container.

10. The information acquisition apparatus according to claim 1,
wherein the container has a curved shape, and
wherein a directional axis of the transducer intersects a center of curvature of the container.

11. The information acquisition apparatus according to claim 1, wherein the container has a semi-spherical shape.

12. The information acquisition apparatus according to claim 1, wherein the acoustic matching member causes the acoustic wave to propagate between the object and the transducer.

13. The information acquisition apparatus according to claim 1, wherein the acoustic matching member deforms in a case where the object presses the acoustic matching member.

14. The information acquisition apparatus according to claim 1, further comprising an optical illumination unit configured to emit light to the object,
wherein the transducer outputs the signal by receiving the acoustic wave generated from the object in response to light emission from the optical illumination unit.

15. The information acquisition apparatus according to claim 1, further comprising an ultrasonic irradiation unit configured to irradiate the object with an ultrasonic wave, wherein the transducer receives the acoustic wave generated from the object in response to emission of the ultrasonic wave from the ultrasonic irradiation unit and outputs the signal.

16. The information acquisition apparatus according to claim 1, further comprising:
an optical illumination unit configured to emit light to the object; and
an ultrasonic irradiation unit configured to irradiate the object with an ultrasonic wave;
wherein the transducer receives a reflected wave of the ultrasonic wave and outputs an echo signal,
wherein the transducer outputs the signal by receiving an acoustic wave generated from the object in response to light emission from the optical illumination unit.

* * * * *